(12) United States Patent
Taylor et al.

(10) Patent No.: US 8,281,423 B2
(45) Date of Patent: Oct. 9, 2012

(54) MULTI-USE PORTABLE HAND HELD HYGIENIC DEVICE

(75) Inventors: Michael Cameron Taylor, Bakersfield, CA (US); Leonard Cameron Taylor, Bakersfield, CA (US)

(73) Assignee: Michael C. Taylor, Bakersfield, CA (US)

( * ) Notice: Subject to any disclaimer, the term of this patent is extended or adjusted under 35 U.S.C. 154(b) by 21 days.

(21) Appl. No.: 12/815,974

(22) Filed: Jun. 15, 2010

(65) Prior Publication Data

US 2011/0302709 A1    Dec. 15, 2011

(51) Int. Cl.
*A47K 3/20* (2006.01)
(52) U.S. Cl. .......................................................... 4/420.4
(58) Field of Classification Search .............. 4/223, 222, 4/224, 228.1, 225.1, 443–448, 420.1–420.5; E03D 9/02
See application file for complete search history.

(56) References Cited

U.S. PATENT DOCUMENTS

| | | | | |
|---|---|---|---|---|
| 1,683,063 A * | 9/1928 | Campus | ........................ | 4/420.5 |
| 2,605,477 A * | 8/1952 | Monserrat | ........................ | 4/448 |
| 2,852,782 A * | 9/1958 | Sundberg | ........................ | 4/420.4 |
| 3,995,326 A * | 12/1976 | Umann | ........................ | 4/420.1 |
| 4,000,742 A * | 1/1977 | Digicomo | ........................ | 604/83 |
| 4,041,553 A * | 8/1977 | Sussman | ........................ | 4/447 |
| 4,092,744 A * | 6/1978 | Butoi | ........................ | 4/447 |
| 4,135,255 A * | 1/1979 | Menendez | ........................ | 4/448 |
| 4,185,187 A * | 1/1980 | Rogers | ........................ | 392/489 |
| 4,205,402 A * | 6/1980 | Miller | ........................ | 4/448 |
| 4,383,339 A * | 5/1983 | Miller | ........................ | 4/448 |
| 4,510,630 A * | 4/1985 | Osgood | ........................ | 4/443 |
| 4,596,058 A * | 6/1986 | Nourbakhsh | ........................ | 4/448 |
| 4,622,704 A * | 11/1986 | Chung | ........................ | 4/443 |
| 4,890,340 A * | 1/1990 | Lovitt | ........................ | 4/443 |
| 4,926,509 A * | 5/1990 | Bass | ........................ | 4/448 |
| 4,995,121 A * | 2/1991 | Barker | ........................ | 4/443 |
| 5,063,618 A * | 11/1991 | Souka | ........................ | 4/420.4 |
| 5,097,540 A * | 3/1992 | Lovitt | ........................ | 4/443 |
| 5,138,726 A * | 8/1992 | Campbell | ........................ | 4/420.4 |
| 5,272,774 A * | 12/1993 | Ivko et al. | ........................ | 4/420.2 |
| D343,447 S * | 1/1994 | Thaler et al. | ........................ | D23/295 |
| 5,495,625 A * | 3/1996 | McGuire | ........................ | 4/420.5 |
| D378,697 S * | 4/1997 | New | ........................ | D23/295 |
| 5,685,028 A * | 11/1997 | Miller et al. | ........................ | 4/443 |
| 5,720,055 A * | 2/1998 | Krist | ........................ | 4/420.4 |
| D400,238 S * | 10/1998 | New | ........................ | D23/295 |
| 6,167,577 B1 * | 1/2001 | Hammad | ........................ | 4/420.4 |
| 6,321,036 B1 * | 11/2001 | Huang | ........................ | 392/453 |
| 6,357,057 B1 * | 3/2002 | Krist | ........................ | 4/420.4 |
| 6,618,865 B1 * | 9/2003 | Kim | ........................ | 4/420.4 |
| 6,628,894 B2 * | 9/2003 | Winter et al. | ........................ | 392/447 |
| 6,675,405 B1 * | 1/2004 | Harm | ........................ | 4/661 |
| 6,691,333 B1 * | 2/2004 | Krist | ........................ | 4/420.4 |
| 6,704,946 B1 * | 3/2004 | Mueller et al. | ........................ | 4/420.4 |
| 6,877,461 B2 * | 4/2005 | Long et al. | ........................ | 122/14.1 |
| 7,013,502 B2 * | 3/2006 | Pacheco | ........................ | 4/420.2 |
| 7,127,750 B2 * | 10/2006 | Lim | ........................ | 4/420.4 |
| 7,913,329 B2 * | 3/2011 | Smith | ........................ | 4/420.4 |
| D641,069 S * | 7/2011 | Sabato | ........................ | D23/233 |
| 2007/0061956 A1 * | 3/2007 | Yu et al. | ........................ | 4/443 |

* cited by examiner

*Primary Examiner* — Lori Baker

(57) ABSTRACT

A multi-functional handheld hygienic device with a J-shaped nozzle and attachment options for alternate use externally on either the genital area as a bidet or the rectal area as a wash and for use internally in the genital area as a douche and the rectal area as an enema. A temperature controlled water tank or water diverter attached to a combined hot and cold faucet supplies temperature controlled water to the nozzle.

13 Claims, 6 Drawing Sheets

MULTI-USE PORTABLE HAND HELD HYGIENIC DEVICE

CROSS-REFERENCE TO RELATED APPLICATIONS

The present utility patent application incorporates by reference applicant's co-pending design patent application Ser. No. 29/348,957 filed Feb. 24, 2010.

STATEMENT REGARDING FEDERALLY SPONSORED RESEARCH OR DEVELOPMENT

Not Applicable.

THE NAMES OF THE PARTIES TO A JOINT RESEARCH OR DEVELOPMENT

Not Applicable.

BACKGROUND OF THE INVENTION

1. Field of the Invention

The present invention relates to hygienic devices, and in particular to a multi-functional handheld hygienic device with a J-shaped spout and attachment options for alternate use in a first position between the legs of a user seated on a toilet as an external bidet or an internal douche or in a second position behind the user seated on a toilet bowl as an external anal cleanser or an internal enema and including a temperature controlled fluid tank to supply the handheld hygienic device.

2. Description of Related Art Including Information Disclosed Under 37 CFR 1.97 and 1.98

In the field of hygienic devices, the benefits of the personal hygiene device known as the bidet, is well known and utilized throughout the world. Although often known as a feminine hygiene device, the bidet is also useful for cleansing the rectal area for any user. The advantages of washing over wiping with tissue for sanitary and medical purposes, has spawned a huge variety of patents for bidet type devices, ranging from the early U.S. Pat. No. 1,683,063 in 1923 with a simple spray bar with hot and cold valves mounted on the toilet bowl, to something similar but with a more complicated mounting system, with U.S. Pat. No. 6,167,577 issued in 2001. There is even an electronic heated seat with warm water nozzle, and warm air blow dry.

Most all of these patented systems, have the same components and function, (turning a toilet into a bidet), with the main difference being how they are attached and operated. And they all also, have the same main drawbacks. They are mounted in or on the bowl of the most unsanitary and hardest to clean plumbing fixture in the world. They have little pressure, or if they do, the nozzle direction is fixed or hard to adjust to where you want it, and they splash water everywhere. Also, if they supply other than cold water, long lines have to be run from hot and cold inlets under the nearest sink, wasting water and time adjusting the temperature every time you use it.

This problem was partially solved with the advent of the hand held bidets, like U.S. Pat. No. 4,510,630 in 1985. Although this unit is not mounted in the bowl, and is much more sanitary, it is still mounted to the side of the toilet, and taps the nearest supply of hot and cold water. This can lead to cold or even worse scalding water, should the pressure suddenly change.

None of these handheld sprayers was really convenient; having to hold the sprayer handle level with or below the toilet seat, adjust the water temperature, and push the water valve on the handle. It is difficult to spray all the desired areas, keep the hose out of the way and not splash through the sides of the seat. The nozzle is really not self-cleaning as it projects the water sideways. The latest patent granted in 2006, U.S. Pat. No. 7,127,750 rehashes all this with another handheld sprayer that attaches to the toilet, but does have a longer, but awkward to operate shaft on the sprayer.

One prior art device (application US2007/0061956) provides a nozzle that simply angles slightly up from the bottom of the sprayer shaft. The prior art does not provide a sufficient nozzle radius to allow the working tip to reach inward while the handle is held vertically.

A previous U.S. Pat. No. 6,628,894 describes a portable warm water heater made of PVC plastic.

What is needed is a handheld personal hygienic device which is easily cleaned and stores away from a toilet and which can perform a number of precisely aimed multi-functional personal hygiene tasks spraying liquid at a controlled temperature and manually controlled pressure.

BRIEF SUMMARY OF THE INVENTION

The present invention solves all of the problems not handled adequately by the prior art devices in a single multi-function device.

An object of the present invention is to provide a handheld personal hygienic device which is easily cleaned and stores away from a toilet and which has a J-shaped nozzle with a vertical handle and adjacent trigger so that the device is easily held by hand in a first position between the legs of a user seated on a toilet to direct a focused flow of genital cleansing fluid aimed precisely where desired on the external genital area as a bidet or internal genital area as a douche, and alternately easily held by hand in a second position behind a user seated on a toilet to direct a focused flow of anal cleansing fluid on the external anal area as an anal cleansing device or internal anal area as an enema, the device being fed by a temperature controlled fluid tank or a diverter on a faucet which allows testing the water temperature prior to diverting the desired temperature water into the hose to perform a number of temperature and pressure controlled (by an operating trigger) precisely aimed multi-functional personal hygiene uses.

In brief, the present invention is a handheld multi-function personal hygiene apparatus which can be used to direct a flow of water for several personal hygiene uses. In a preferred embodiment of the invention, the hand held bidet apparatus comprises a handle with a trigger controlled valve for controlling the flow and pressure of water through a J-shaped nozzle attached to the handle which allows the user to easily direct the nozzle tip to the desired area, with the advantage of not only cleansing the anal and or genital area, but also serving as a non-invasive douche or enema. This is accomplished by placing the specially structured tip of the nozzle at the entrance to the vagina or anus, and triggering enough water flow and pressure for the fountain to penetrate into the cavity and clean internally as well as lubricate the anal tract to facilitate a bowel movement.

The nozzle tip also is designed to allow easy attachment of disposable plastic douche and enema tips for a conventional deep penetration type douche or enema. The device is designed to stand alone, not be attached to the toilet, so that it stays more sanitary, and does not interfere with the cleaning of the toilet, as do most all other bidets, which attach to the seat or tank or rim in some fashion. A low wattage, low amperage warm water heater has also been designed to work with this device, to provide instant warm water and ease of use.

A quick connect diverter, which attaches to the nearest faucet and allows for testing the water temperature prior to diverting the heated water at the desired temperature through the hose, will also be provided for those bathrooms equipped with point of use water heaters, or similar circulating devices which also provide instant warm water, eliminating the need for the bidet water heater.

The diverter attaches to the average bathroom faucet by unscrewing the aerator and replacing it with the diverter. The hose is attached to the side of the diverter with an air hose type quick-connect and when the faucet is turned on and the desired water temperature is reached, a button or lever is pushed on the diverter, and the water stops flowing into the sink and is diverted to the hose.

The main advantage of the present invention is that it solves many of the problems of prior art devices with a single handheld multi-functional device.

Problem 1. Cleanliness: The present invention is standalone, and does not attach to the toilet in any way. It is made to hang on the wall behind or beside the toilet, often next to the tissue holder, so the normal cleaning of the toilet is not interfered with in any way, and the wand tip is not exposed to the bacteria and germs of the bowl. By allowing the water to wash over the tip for a few seconds after use, and self-clean, it actually stays more hygienic than the average showerhead.

Problem 2. Directing the spray: The ergonomic handle of the present invention is easy to hold with the trigger controlled by the forefinger (instead of a thumb button for volume control) to allow a user to easily adjust the flow from a trickle to a 6-inch high fountain. The unique J-shaped nozzle of the present invention allows the user to easily slip the wand in the front or back of the toilet seat while sitting on it, and place the tip of the nozzle exactly where they want it, with the handle conveniently high, dry, and vertical while the J-nozzle allows the tip to reach further back with the handle held in a relatively vertical position.

Problem 3. Functionality: The chromed J-shaped nozzle of the present invention simply has at most a 6 mm hole in the tip. It has no little spray holes or slots to plug, like all the other sprayers, and the size and shape allow the water jet to be used safely and efficiently as a non-invasive enema, or douche, or simply to wash the area. This is how it works: The J-shaped nozzle allows the user to place the nozzle at the entrance of the anus or vagina, and trigger the stream of water with enough pressure to go up inside and gently clean. It provides the convenience of being able to feel refreshed in a few seconds, without the hassle and expense of disposable douche bottles, with their 4-inch long nozzle that must be pushed up inside the vagina to work.

For internal and external anal cleaning, with the present invention in a few seconds, any user feels relieved, and clean inside and out.

Children can become so constipated, that trying to force a conventional enema up inside them is painful and they cry. With the present invention, the child sits on the toilet, and the warm water works its way up inside to lubricate and within seconds they are painlessly going.

The uses in nursing homes and hospitals, for this economical, simple, yet effective device with disposable sanitized heads would be numerous.

Problem 4. Water temperature: Although the J-shaped nozzle liquid spray device of the present invention may be offered separately, to be attached to faucets, and cold water supply lines like other units with a simple "T" valve, it is designed to work best with its "point of use" warm water heater. This small heater which will be approximately 9 inches tall by 4 inches wide, by 3 inches deep, (about the size of a good book), contains about 1½ liters of water, and will be very "green". Since it heats such a small amount of water, it will use the energy of a small light bulb. Also the water will never be too hot. The preset temperature of the water will only be 90 to 99 degrees F., and will be constant with no risk of scalding with a failsafe upper temperature limit of 105 degrees F. Since the directed spray of the present invention is so efficient, the average wash time is less than 15 seconds. Thus, the water use is low, energy use is low and the average household will save on toilet tissue. A user can afford the best tissue because so little is necessary to pat the area dry. No wiping or cleaning is necessary. The 6 mm supply hose from the tank may be less than 3 feet long, so there is only a few seconds, of letting the wand clean itself, before the water is warm for use. The water tank is preferably thermoplastic, rugged and durable, for no scaling, and elimination of shock potential in the event of catastrophic failure of the heating element.

A advantage of the present invention is that it provides a handheld personal hygiene device which can by precisely aimed and temperature controlled for multi-functional personal hygiene uses, including a bidet, a vaginal douche, an anal spray wand, and an enema spray wand.

A related advantage of the present invention is that it can be used as a non-invasive enema or douche.

BRIEF DESCRIPTION OF THE SEVERAL VIEWS OF THE DRAWINGS

These and other details of the present invention will be described in connection with the accompanying drawings, which are furnished only by way of illustration and not in limitation of the invention, and in which drawings.

DETAILED DESCRIPTION OF THE INVENTION

In FIGS. 1-8, a handheld multi-functional personal hygiene cleaning device 10 comprises a liquid spray device 30 having a J-shaped nozzle 34 and a liquid heater tank 20.

Figure 3:
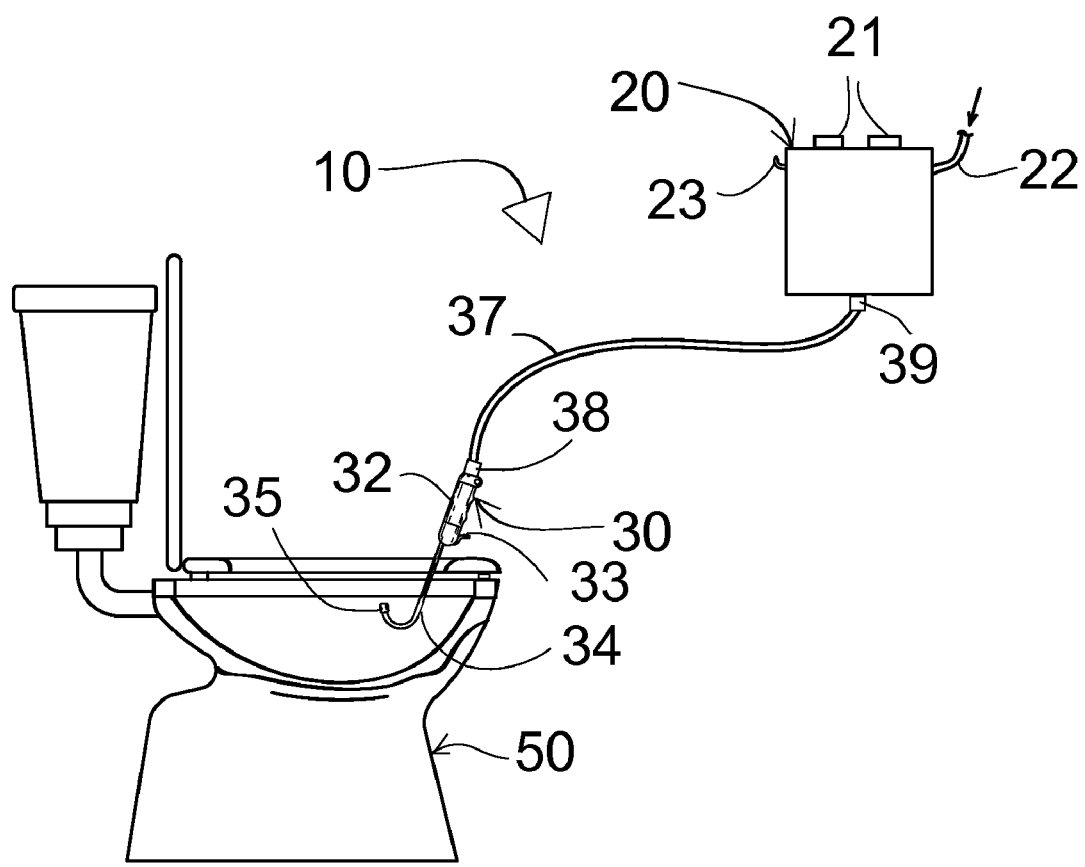
FIG. 3 is a side elevational view in partial section showing the liquid spray device positioned in a front portion of a toilet bowl with the J-shaped nozzle pointing backward for use as a bidet or cleansing douche.
Figure 4:
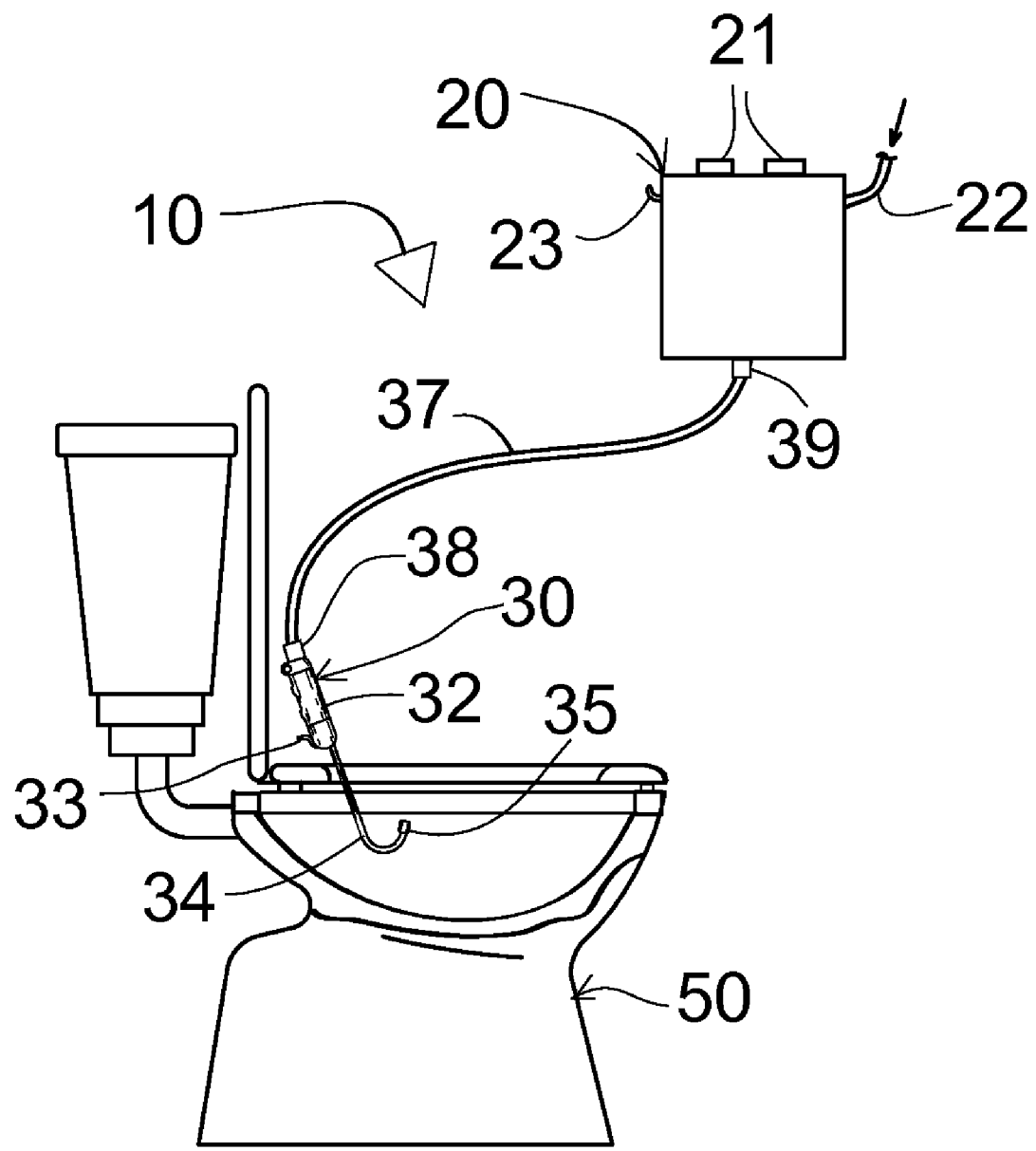
FIG. 4 is a side elevational view in partial section showing the liquid spray device positioned in a back portion of a toilet bowl with the J-shaped nozzle pointing forward for use as an anal cleansing spray or an enema.
Figure 5:
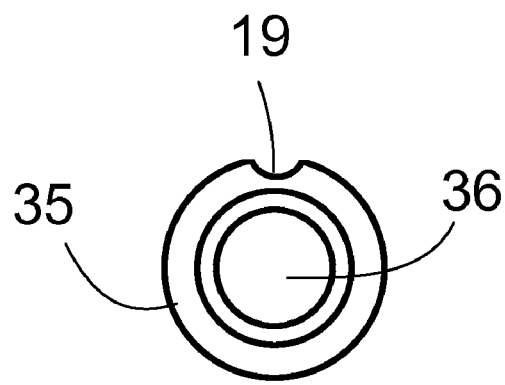
FIG. 5 is a plan view of the distal tip of the J-shaped nozzle showing the U-shaped groove in the perimeter head for receiving and securing any of a variety of standard spray heads for different functions.
Figure 6:
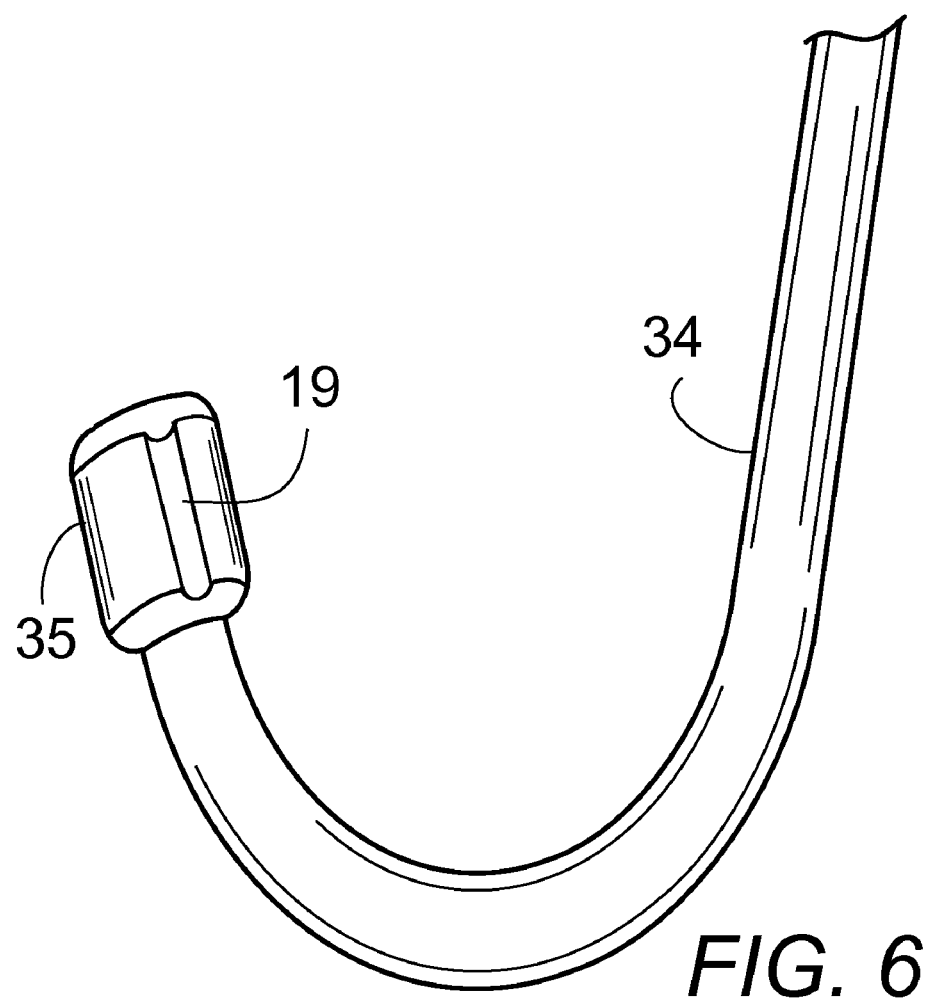
FIG. 6 is a partial perspective view of the distal tip of the J-shaped nozzle showing the U-shaped groove in the perimeter head for receiving and securing any of a variety of standard spray heads for different functions.

The liquid spray device 30 comprises a J-shaped nozzle 34 held by hand in a first position between the legs of a user seated on a toilet as shown in FIG. 3, to spray a genital cleansing liquid from the nozzle externally to a genital area of the user as a bidet and alternately to spray a douching liquid internally in the genital area as a douche without full insertion of the nozzle, and held by hand in a second position behind a user seated on a toilet, as shown in FIG. 4, to apply spray a cleansing liquid externally to a rectal area as a rectal wash and alternately to spray an enema liquid internally in the rectal area as an enema without full insertion of the nozzle. A handle 32 at a proximal end of the nozzle is grasped by the user. A trigger 33 in proximity to the handle manually controls the spray. The trigger 33 is positioned on a side of the handle opposite to the J-shaped nozzle 34 for ease of operation in both the first and second positions. A tip opening 36 on the distal end of the J-shaped nozzle is a small diameter opening which allows a narrow concentrated spray of liquid.

At least one means for receiving a variety of spray attachments to an external perimeter head 35 around the tip opening 36 for altering the spray for a variety of different uses.

The means for receiving a variety of spray attachments preferably comprises a U-shaped groove 19 on a side of the tip end head 35 to secure any of a variety of standard small standard sanitary disposable nozzles removably attached to the tip end 35 communicating with the U-shaped groove 19 so that a new sanitary disposable nozzle can be applied for each usage.

The standard small standard sanitary disposable nozzles may comprise a small standard sanitary disposable douche nozzle, a standard small sanitary disposable enema nozzle, a standard small sanitary disposable bidet spray nozzle, a small standard sanitary disposable anal spray nozzle, or any other desired small standard sanitary disposable spray nozzle attachable to the tip end communicating with the U-shaped groove 19 so that a new sanitary disposable anal spray nozzle can be applied for each usage.

A flexible hose 37 extends from the proximal end of the liquid spray device 30 to the means for connecting to a liquid supply to provide a steady flow of liquid of a desired temperature to the J-shaped liquid spray nozzle 43. The hose 37 is sufficiently long and flexible so that the liquid spray device can be moved between the first position and the second position. The hose 37 preferably comprises two layers of reinforced polyurethane hose, a reinforced inner hose covered by a reinforced outer layer forming a soft flexible hose to enable manipulation of the J-shaped liquid spray nozzle for the different positions and uses. The hose preferably has standard USA plumbing compression fittings 38, 39, and 39A on the ends so that the hose holds up under continuous pressure, provides a reliable high-pressure seal, has a smooth easy to clean surface, and is easy to replace.

Figure 7:
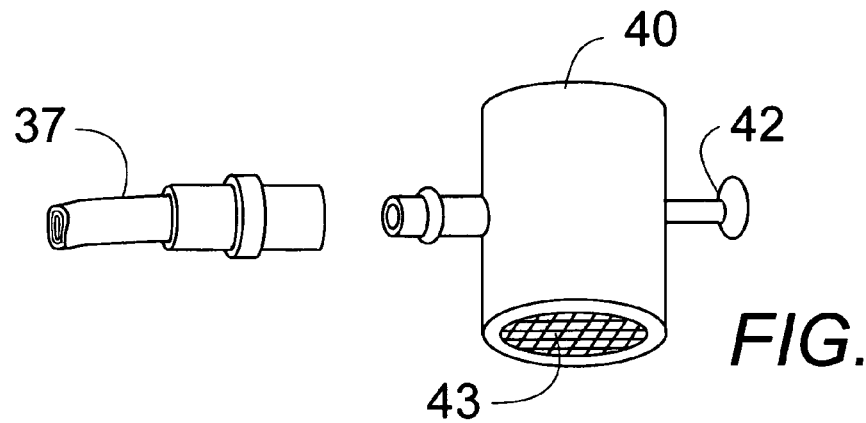
FIG. 7 is an exploded perspective view of the diverter head of the present invention with the hose aligned for attachment.
Figure 8:
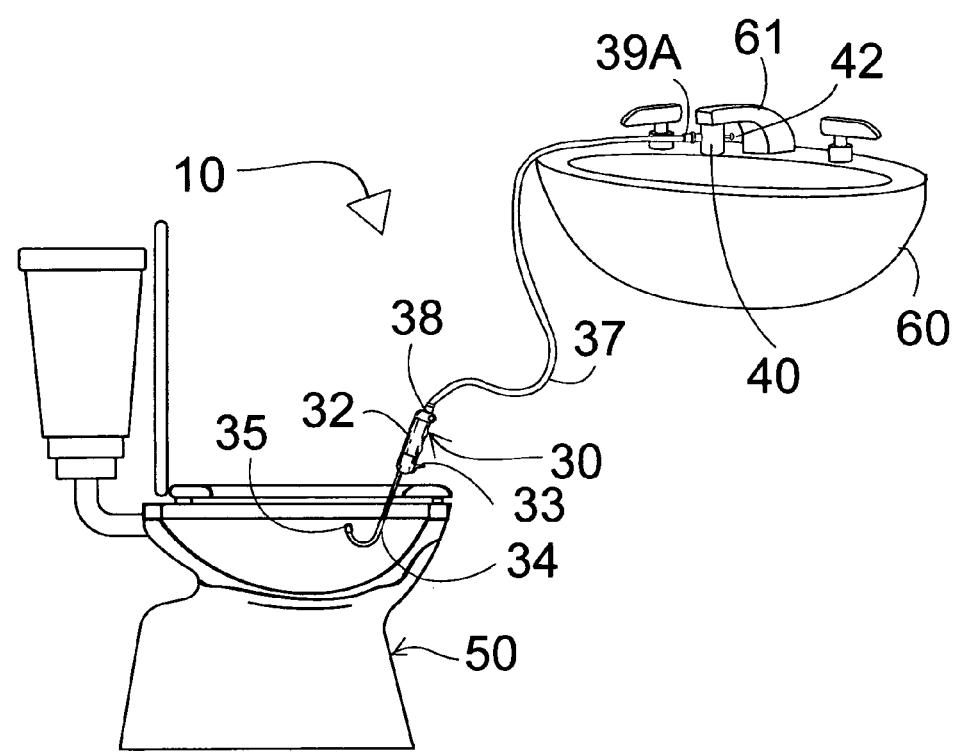
FIG. 8 is a perspective view of the liquid spray device of the present invention positioned in a front portion of a toilet bowl with the J-shaped nozzle pointing backward for use as a bidet or cleansing douche and the diverter head of FIG. 7 attached to a sink faucet adjacent to the toilet.

In FIGS. 7 and 8, the means for connecting to a liquid supply comprises a liquid diverter 40 having a protruding quick connect male coupler to receive a female coupler 39A at the end of the hose 37. The diverter 40 attaches to a bathroom faucet 61 in place of a bathroom faucet aerator on a bathroom tub or sink 60. The diverter 40 has a control 42 set in a first position to allow water to flow from the faucet into the drain through the bottom screen 43 to adjust the temperature of the water to a desired level by adjusting the mix of hot and cold water and set in a second position to divert the desired temperature water to flow into the hose 37 to the J-shaped liquid spray nozzle 30.

Figure 1:
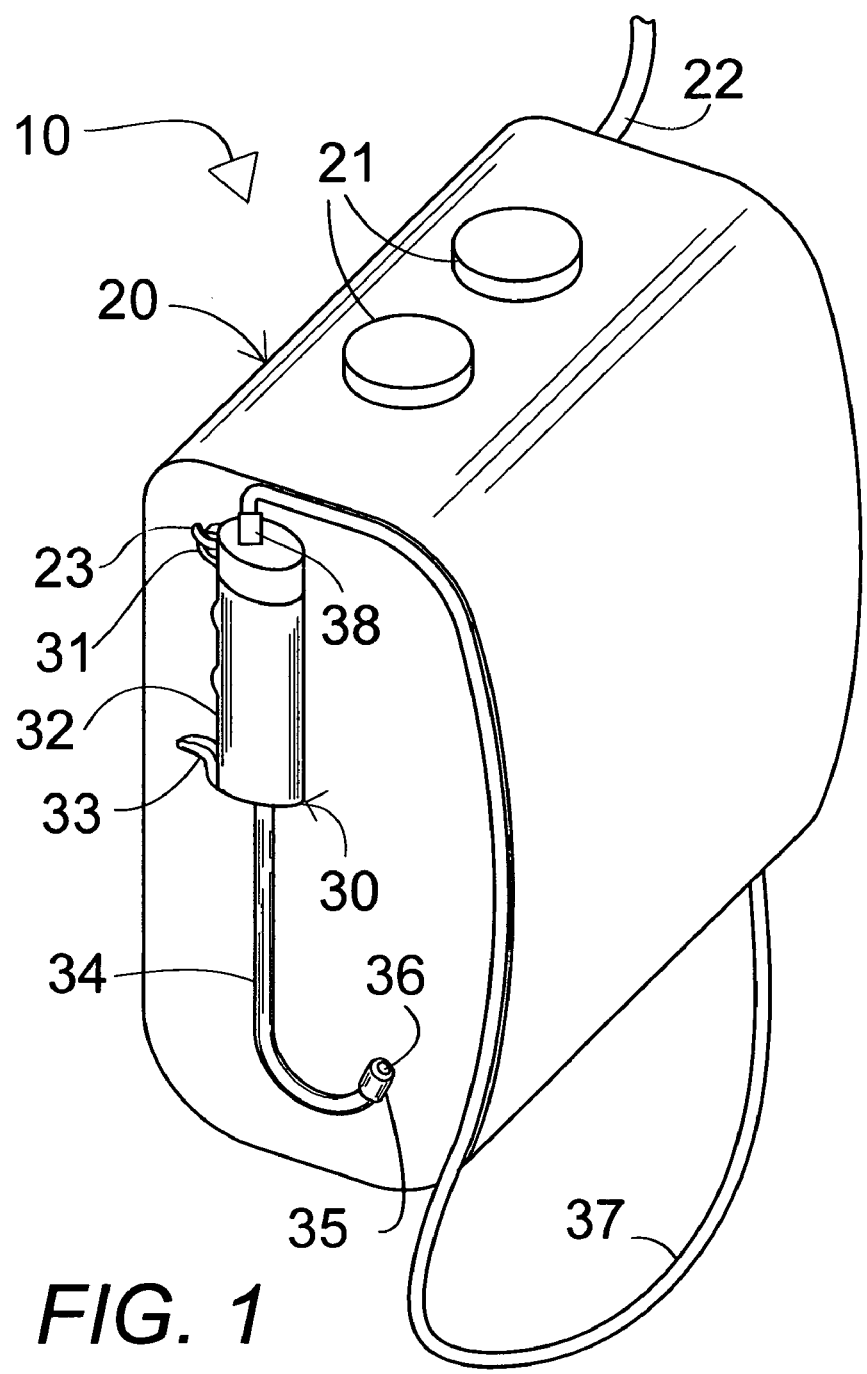
FIG. 1 is a perspective view showing the multi-functional hygiene cleaning device of the present invention showing the J-shaped nozzle of the liquid spray device hooked onto the liquid heater tank with the connecting hose therebetween.
Figure 2:
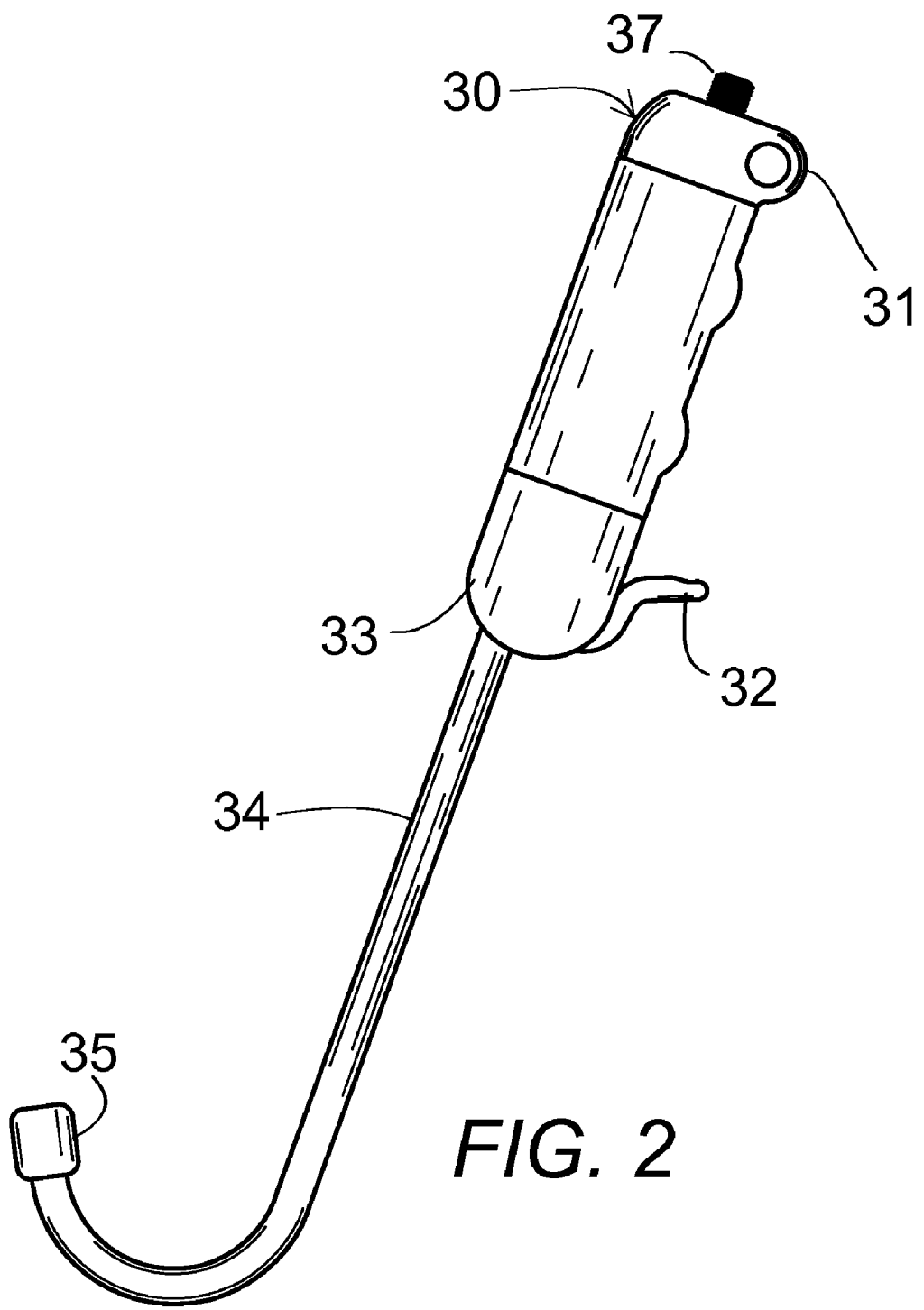
FIG. 2 is a side elevational view of the liquid spray device having the J-shaped nozzle, the handle, and the trigger.

In FIGS. 1, 3, and 4, the means for connecting to a liquid supply comprises at least one liquid heater tank 30 attached to a wall adjacent a toilet 50, having controls 21 and a hose 22 to a water supply, contains and dispenses a liquid at a controlled temperature through a hose 37 for transmitting the liquid from the tank 20 to the liquid spray device 30. The tank 20 is positioned adjacent to the toilet 50 and the hose 37 is sufficiently long and flexible so that the liquid spray device 30 can be moved between the first position of FIG. 3 and the second position of FIG. 4.

The tip opening 36 comprises at most a 3-6 mm interior diameter opening to produce a focused concentrated spray.

The external size of the tip perimeter head 35 around the tip opening 36 of the liquid spray device 30 comprises an outer diameter of at most 15 mm outer diameter to prevent a seal in a vaginal opening to prevent a dangerous level of internal water pressure and prevent a seal in an anal opening to prevent too much water pressure to enter the rectum and thereby prevent rupture damage.

A loop 31 on the proximal end of the handle 32 removably hangs on a hook 23 extending from the heater tank 20.

The liquid heater tank 20 comprises a liquid heater tank having a preset thermostat having a maximum temperature limit of 105 degrees F. to prevent scalding the user with adjustment knobs 21 to control the tank. The heater tank 20 preferably uses 115 volt A.C., with a 4 amps or less heating element with grounded 3-prong plug, factory preset to 105 degrees F. or less, maximum temperature, using 400 watts or less power. Preferably, the tank is made of plastic for home use and stainless steel for health care facilities with as on-off switch, and limited range heat control, and factory preset thermostat to maintain the liquid temperature as less than 105 degrees F.

In use, the liquid spray device 30 is held between the legs of the user, as in FIG. 3, for use as a bidet or douche and alternately held behind the user, is in FIG. 4, for use as an anal spray cleanser or an enema spray.

For hospitals and other health care facilities, disposable sanitized spray nozzles may be attached to the tip of the spray device similar to the way to the twist off tips on the ear and nose lights used by doctors.

It is understood that the preceding description is given merely by way of illustration and not in limitation of the invention and that various modifications may be made thereto without departing from the spirit of the invention as claimed.

What is claimed is:

1. A handheld multi-functional personal hygiene device comprising:

a J-shaped liquid spray nozzle comprising a straight portion having a handle at a proximal end for grasping by a user seated on a toilet seat, the straight portion held by the user in a substantially vertically downward orientation with the handle above the toilet seat and the straight portion extending down below the user; a curved portion at a distal end extending from the straight portion and curving upwardly to position a distal end of the curved portion pointing in a substantially vertically upward orientation, the handle held above the toilet with the straight portion extending down below a crotch area of the user's body; the upwardly curved portion having a tip opening on the distal end to emit a narrow concentrated spray of liquid aimed vertically upward at a desired portion of the crotch area of the user's body; a trigger in proximity to the handle for manually controlling spray pressure, the trigger positioned on a side of the handle opposite to the upwardly curved distal end for ease of operation; the J-shaped liquid spray nozzle held by hand in a first position between the legs of a user seated on a toilet to spray a genital cleansing liquid from the nozzle externally to a genital area of the user functioning as a bidet spray, and alternately to spray a douching liquid internally in the genital area functioning as a douche spray without full insertion of the nozzle, and held by hand in a second position behind a user seated on a toilet to spray a cleansing liquid externally to a rectal area functioning as a rectal wash spray and alternately to spray an enema liquid internally in the rectal area functioning as an enema spray without full insertion of the nozzle;

an external perimeter head around the tip opening and at least one spray nozzle receiving adaptor associated with the external perimeter head for receiving any of a variety of existing standard spray nozzle attachments to an external perimeter head around the tip opening for altering the spray for a variety of different uses;

a flexible hose extending from the proximal end of the J-shaped liquid spray nozzle to a means for connecting to a liquid supply to provide a steady flow of liquid of a desired temperature to the J-shaped liquid spray nozzle, the hose being sufficiently long and flexible so that the liquid spray device can be moved between the first position and the second position; thereby providing a hand-held multi-functional personal hygiene device.

2. The device of claim 1 wherein the means for connecting to a liquid supply comprises a liquid diverter that attaches to a bathroom faucet in place of a bathroom faucet aerator, the diverter having a control set in a first position to allow water to flow from the faucet into the drain to adjust the temperature of the water to a desired level by adjusting the mix of hot and cold water and set in a second position to divert the desired temperature water to flow into the hose to the J-shaped liquid spray nozzle.

3. The device of claim 1 wherein the means for connecting to a liquid supply comprises at least one liquid heater tank for containing and dispensing a liquid at a controlled temperature, the tank positioned adjacent to the toilet.

4. The device of claim 3 wherein the at least one liquid heater tank comprises a liquid heater tank having a preset thermostat having a maximum temperature limit of 105 degrees F. to prevent scalding the user.

5. The device of claim 3 wherein the at least one liquid heater tank further comprises a hook for retaining the liquid spray device when not in use.

6. The device of claim 1 wherein the hose comprises two layers of reinforced polyurethane hose, a standard existing reinforced inner hose covered by a reinforced outer layer forming a soft flexible hose to enable manipulation of the J-shaped liquid spray nozzle for the different positions and uses, the hose having standard plumbing compression fittings on the ends to sustain continuous pressure and to provide a high-pressure seal, the hose having a smooth surface, and the hose being replaceable.

7. The device of claim 1 wherein the tip opening comprises a single orifice with an inside diameter of at most a 3-6 mm to produce an optimum focused spray of liquid.

8. The device of claim 1 wherein the external perimeter head around the tip end of the tip opening of the liquid spray device comprises an outer diameter of at most 15 mm outer diameter to prevent a seal in a vaginal opening to limit internal water pressure and prevent a seal in an anal opening to limit water pressure in the rectum and thereby prevent rupture damage.

9. The device of claim 1 wherein the spray nozzle receiving adaptor comprises a U-shaped groove on a side of the external perimeter head for removably receiving a small sanitary existing standard disposable douche nozzle attachable to the external perimeter head communicating with the U-shaped groove so that a new sanitary disposable douche nozzle can be applied for each usage.

10. The device of claim 1 wherein the spray nozzle receiving adaptor comprises a U-shaped groove on a side of the external perimeter head for removably receiving a small sanitary existing standard disposable enema nozzle attachable to the external perimeter head communicating with the U-shaped groove so that a new sanitary disposable enema nozzle can be applied for each usage.

11. The device of claim 1 wherein the spray nozzle receiving adaptor comprises a U-shaped groove on a side of the external perimeter head for removably receiving a small sanitary existing standard disposable bidet spray nozzle attachable to the external perimeter head communicating with the U-shaped groove so that a new sanitary disposable bidet spray nozzle can be applied for each usage.

12. The device of claim 1 wherein the spray nozzle receiving adaptor comprises a U-shaped groove on a side of the external perimeter head for removably receiving a small sanitary existing standard disposable anal spray nozzle attachable to the external perimeter head communicating with the U-shaped groove so that a new sanitary disposable anal spray nozzle can be applied for each usage.

13. The device of claim 1 further comprising a hook engaging loop on the proximal end of the handle for hanging the liquid spray device on a hook positioned away from the toilet when not in use.

* * * * *